(12) United States Patent
Xie et al.

(10) Patent No.: US 12,109,133 B2
(45) Date of Patent: Oct. 8, 2024

(54) WEAVING METHOD FOR NASAL SINUS STENT AND STENT OBTAINED THEREOF

(71) Applicant: PUYI (SHANGHAI) BIOTECHNOLOGY CO., LTD., Shanghai (CN)

(72) Inventors: Jian Xie, Shanghai (CN); Zheng Wei, Shanghai (CN)

(73) Assignee: PUYI (SHANGHAI) BIOTECHNOLOGY CO., LTD., Shanghai (CN)

( * ) Notice: Subject to any disclaimer, the term of this patent is extended or adjusted under 35 U.S.C. 154(b) by 1195 days.

(21) Appl. No.: 16/306,885

(22) PCT Filed: Jun. 3, 2016

(86) PCT No.: PCT/CN2016/084612
§ 371 (c)(1),
(2) Date: Dec. 30, 2020

(87) PCT Pub. No.: WO2017/206155
PCT Pub. Date: Dec. 7, 2017

(65) Prior Publication Data
US 2021/0121308 A1    Apr. 29, 2021

(51) Int. Cl.
*A61F 2/90* (2013.01)
*D03D 1/00* (2006.01)
(Continued)

(52) U.S. Cl.
CPC ............... *A61F 2/90* (2013.01); *D03D 1/00* (2013.01); *D04C 1/06* (2013.01); *D04C 3/48* (2013.01);
(Continued)

(58) Field of Classification Search
None
See application file for complete search history.

(56) References Cited

U.S. PATENT DOCUMENTS 5,476,027 A * 12/1995 Uchida ............... D04C 3/48
87/29
6,007,574 A * 12/1999 Pulnev ............... A61F 2/01
623/1.15

(Continued)

*Primary Examiner* — Jocelyn Bravo
(74) *Attorney, Agent, or Firm* — Dickinson Wright PLLC (57) ABSTRACT

The present invention relates to a braiding method for a nasal sinus stent, comprising: providing a filament; providing a braiding tool having a longitudinal central axis, wherein the braiding tool comprises a first shaping part and a second shaping part which are axially spaced from each other, wherein the first shaping part is provided with n first anchor points, and the second shaping part is provided with n second anchor points; forming an initial configuration stent by around a circumferential direction of the braiding tool, allowing a single filament starting from 1st first anchor point on the first shaping part, coming across m1 vertex intervals to extend towards the second anchor point, and then coming across m2 vertex intervals to extend towards the first anchor point, so as to complete a first "V" shaped braiding path, and then repeating the "V" shaped braiding path until the single filament returns to the 1st first anchor point, wherein the initial configuration stent has a circumference and n vertices with vertex interval obtained by dividing the circumference by n; m1 and m2 are integral multiples of 0.5, the sum of m1+m2 is an integer, and the sum of m1+m2 is not an integral multiple of a divisor of n. The sinus stent obtained by the above braiding method has good shape adaptability and is particularly suitable for being used as a self-expanding stent in the nasal cavity.

12 Claims, 8 Drawing Sheets

(51) Int. Cl.
*D04C 1/06* (2006.01)
*D04C 3/48* (2006.01)
*D03D 49/26* (2006.01)

(52) U.S. Cl.
CPC ........ *A61F 2240/001* (2013.01); *D03D 49/26* (2013.01); *D10B 2509/06* (2013.01)

(56) References Cited

U.S. PATENT DOCUMENTS

| | | | | |
|---|---|---|---|---|
| 6,622,604 | B1* | 9/2003 | Chouinard | D04C 1/06 87/8 |
| 6,652,571 | B1* | 11/2003 | White | A61F 2/90 623/1.53 |
| 6,792,979 | B2* | 9/2004 | Konya | A61F 2/88 140/92.1 |
| 7,101,392 | B2* | 9/2006 | Heath | A61B 90/39 623/1.34 |
| 9,155,643 | B2* | 10/2015 | Clerc | D04C 1/06 |
| 9,381,328 | B2* | 7/2016 | Xie | A61M 25/1006 |
| 2002/0147489 | A1* | 10/2002 | Hong | A61F 2/90 623/1.2 |
| 2003/0153973 | A1* | 8/2003 | Soun | D04C 3/48 623/1.53 |
| 2005/0283962 | A1* | 12/2005 | Boudjemline | D04C 1/06 29/433 |
| 2006/0116752 | A1* | 6/2006 | Norton | D04C 1/02 623/1.34 |
| 2009/0198315 | A1* | 8/2009 | Boudjemline | D04C 3/48 623/1.2 |
| 2010/0191319 | A1* | 7/2010 | Lilburn | A61F 2/82 87/8 |
| 2011/0265908 | A1* | 11/2011 | Clerc | D04C 7/00 29/559 |
| 2012/0271403 | A1* | 10/2012 | Gries | D04C 3/48 87/9 |
| 2012/0310319 | A1* | 12/2012 | Tieu | A61F 2/945 623/1.4 |
| 2013/0060323 | A1* | 3/2013 | McHugo | A61F 2/90 623/1.18 |
| 2013/0092013 | A1* | 4/2013 | Thompson | D04C 3/42 87/9 |
| 2014/0058436 | A1* | 2/2014 | Rosenbluth | A61B 17/12172 606/200 |
| 2015/0045874 | A1* | 2/2015 | McMahon | A61F 2/90 623/1.22 |
| 2016/0213498 | A1* | 7/2016 | Wang | D04C 3/48 |
| 2020/0229955 | A1* | 7/2020 | Uesugi | D04C 1/02 |
| 2021/0100667 | A1* | 4/2021 | Ngo | D04C 3/48 |
| 2022/0119997 | A1* | 4/2022 | Steinhilber | A61F 2/90 |
| 2023/0011914 | A1* | 1/2023 | Lu | D04C 3/40 |

* cited by examiner

WEAVING METHOD FOR NASAL SINUS STENT AND STENT OBTAINED THEREOF

BACKGROUND OF THE INVENTION

1. Field of the Invention

The present invention relates generally to a nasal sinus stent, and more particularly to a braiding method for a nasal sinus stent and a stent obtained thereof.

2. Related Art

It is well known that stents can be used to hold, open or enlarge body structures such as veins, arteries, ureters, urethras, hollow-body organs, nasal passages, sinus cavities, and the like.

There are many folds inside the nasal cavity. The shape of the nasal cavity is variable. The individual differences of the nasal cavity are very large. The complexity of the internal space of the nasal cavity is further aggravated if there is a lesion. In fact, the internal space of the nasal cavity may be as a cone, a trapezoidal body, a rhomboid, an ellipsoid or a sphere, or a variation and combination thereof, or even an irregular body.

CN101945621B discloses a stent, which is capable of biodegrading, and has a first compressed configuration enabling low profile delivery through a delivery device and a second expanding configuration for apposition against tissue. Specifically, the stent comprises at least one filament, which is formed into a shape having a series of peaks and valleys, and the shape approximates a repeating diamond-shaped pattern. At least one of the peaks and valleys has a loop at an end thereof, which is formed by winding the at least one filament.

Studies show that the stent of above patent is generally in the shape of a diamond or a crown in the second expanding configuration, and its cross section is limited to an approximately circular shape. Although it can be effectively applied to the blood circulation system, it cannot be adapted to the ever-changing internal space of the nasal cavity, resulting in a poor adaptability.

SUMMARY OF THE INVENTION

In order to solve the problem of the poor adaptability of the prior art nasal sinus stent, the present invention aims to provide a braiding method for a nasal sinus stent and a stent obtained thereof.

The present invention provides a braiding method for a nasal sinus stent comprising: providing a filament; providing a braiding tool having a longitudinal central axis, wherein the braiding tool comprises a first shaping part and a second shaping part which are axially spaced from each other; wherein the first shaping part is provided with n uniformly-spaced first anchor points for hooking the filament in a first cross section perpendicular to the longitudinal central axis; the second shaping part is provided with n uniformly-spaced second anchor points for hooking the filament in a second cross section perpendicular to the longitudinal central axis; wherein n is an integer in 3-59; forming an initial configuration stent by around a circumferential direction of the braiding tool, allowing a single filament starting from 1st first anchor point on the first shaping part, coming across m1 vertex intervals to extend towards the second anchor point, and then coming across m2 vertex intervals to extend towards the first anchor point, so as to complete a first "V" shaped braiding path, and then repeating the "V" shaped braiding path until the single filament returns to the 1st first anchor point, wherein the initial configuration stent has a circumference and n vertices with vertex interval obtained by dividing the circumference by n; m1 and m2 are integral multiples of 0.5, the sum of m1+m2 is an integer, and the sum of m1+m2 is not an integral multiple of a divisor of n.

The nth first anchor point in the first anchor points is staggered or aligned with the nth second anchor point in the second anchor points on a cylindrical surface.

The nth first anchor point in the first anchor points is staggered or aligned with the nth second anchor point in the second anchor points on a lateral face of a conical frustum.

An imaginary line connecting the nth first anchor point in the first anchor points to the nth second anchor point in the second anchor points is parallel to the longitudinal central axis.

When m1=m2, n is an odd number in 3-59.

An imaginary line connecting a midpoint of an imaginary line connecting the (n−1)th first anchor point in the first anchor points to the nth first anchor point to the (n−1)th second anchor point in the second anchor points is parallel to the longitudinal central axis.

The filament is monofilament or a strand forming by swirling at least two monofilaments with each other.

The braiding tool further comprises a connecting part, wherein the first shaping part is connected to the second shaping part by the connecting part to be fixed at a predetermined place.

The braiding tool further comprises a hoop around and spaced from the connecting part.

The single filament starts from the 1st first anchor point on the first shaping part, comes across m1 vertex intervals to extend towards the second anchor point between the connecting part and the hoop, comes across m2 vertex intervals to extend towards the first anchor point between the connecting part and the hoop, so as to complete a first "V" shaped braiding path, and then repeats the "V" shaped braiding path until the single filament returns to the 1st first anchor point to form the initial configuration stent.

An end-to-end connection is provided by parallel double lines formed from ends of the single filament.

The filament has intersections connected by polymer glue.

The present invention also provides a nasal sinus stent according to above method, wherein the nasal sinus stent is formed by a plurality of the "V" shaped braiding path, each of which comprises vertices and supporting rods symmetrically arranged at both sides of the vertices.

A braiding angle of the supporting rod is within 20°-70°.

A vertex angle between two supporting rods is within 40°-140°.

An outer diameter of the filament is within 0.05-3 mm, and a bending radius of the vertex is 0.5-6 times the outer diameter of the filament.

The vertex is a curved portion, a composite vertex, a negative loop vertex, a positive loop vertex, or a tridimensional vertex.

The aspect ratio is within 0.1-1.9.

A profile of the nasal sinus stent is the same as that of the braiding tool.

The obtained nasal sinus stent according to the braiding method of the present invention has good shape adaptability, and is particularly suitable for use as a self-expanding stent in the nasal cavity. The nasal sinus stent provided by the present invention can be uniformly compressed to the first compressed configuration through the filament regular parallelogram cells. When the stent is released at the nasal cavity, the stent in the second expanding configuration can adapt to a variety of inner cavities for apposition against tissues.

BRIEF DESCRIPTION OF THE DRAWINGS

FIG. 8b shows a deformation of the vertex in FIG. 8a;
FIG. 8b shows another deformation of the vertex in FIG. 8a;
FIG. 8c shows yet another deformation of the vertex in FIG. 8a;
FIG. 8d shows yet another deformation of the vertex in FIG. 8a;
FIG. 8e shows the other deformation of the vertex in FIG. 8a.

DESCRIPTION OF THE PREFERRED EMBODIMENTS

In connection with appended figures, preferred embodiments of the present invention are provided and described in details.

Embodiment 1

Figure 3:
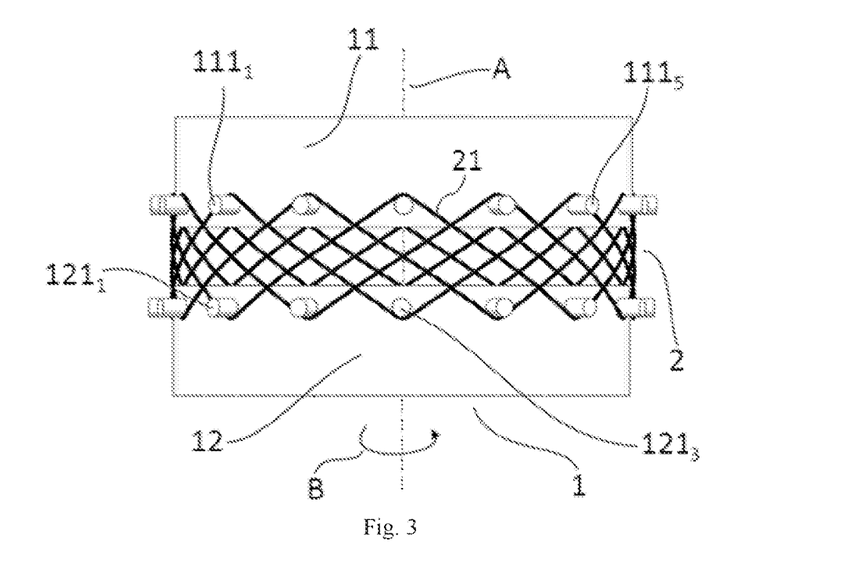
FIG. 3 shows a nasal sinus braiding around the braiding tool in FIG. 1.

The braiding method for a nasal sinus stent provided by the present invention comprises of providing filament 21 (referring to FIG. 3). The filament 21 can be monofilament or a strand, which is formed by swirling at least two monofilaments with each other. Preferably, the at least two monofilaments have the same denier in a length direction. In one preferred embodiment, the strand is well cohesive and can't be easily separated into the monofilaments before swirling. In which, the monofilament may be the polymer filament mentioned in CN101945621B, which may comprise the mentioned metallic region, flexible section and etc, which is incorporated herein by reference in its entirety. In fact, the filament 21 may be from a degradable material, or a non-degradable material. The degradable material may be a degradable polymer material, or a degradable metal material. In which, the degradable polymer material may be selected from: polylactic acid (PLA), polyLlactic acid (PLLA or LPLA), polyglycolic acid/polylactic acid (PGLA), polycaprolactone (PCL), polyhydroxylbutyratevalerate (PHBV), polyacetylglutamicacid (PAGA), polyorthoesters (POE) and polyethylene oxide/polybutylene terephthalate (PEO/PBTP), poly-p-dioxanone (PPDO), Poly(butylene succinate) (PBS), poly(glycerol sebacate) (PGS), chitosan, PVA and copolymers or blends thereof. The degradable metal material may be selected from: magnesium metal, magnesium alloy, zinc-based alloy, iron, iron-base alloy, tungsten and tungsten-base alloy.

Figure 1:
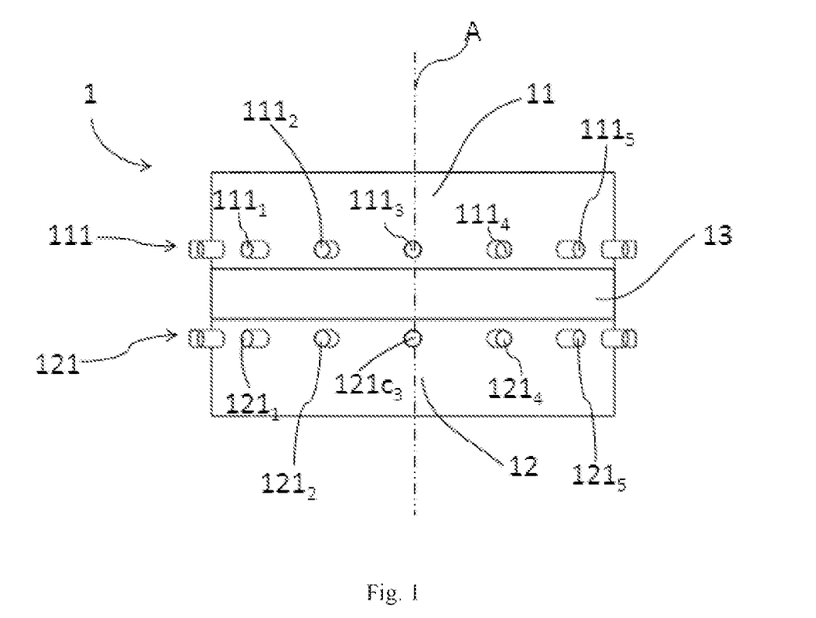
FIG. 1 is an overall structure diagram of the braiding tool according to the present invention.
Figure 2:
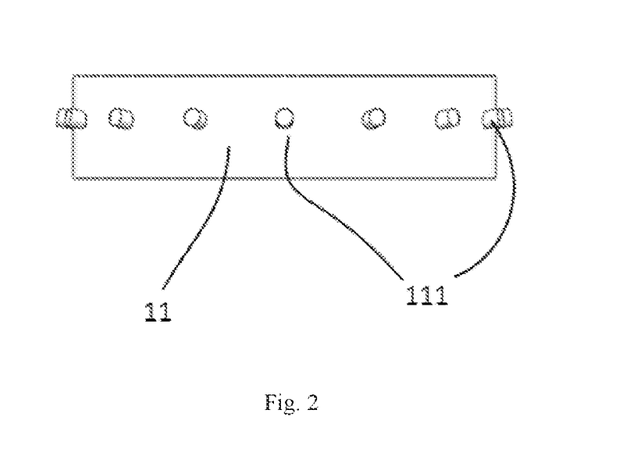
FIG. 2 shows the upswept anchor point of the braiding tool in FIG. 1.

The braiding method for the nasal sinus stent provided by the present invention further comprises of providing a braiding tool for determining the final shape of the nasal sinus stent of the present invention. The braiding tool 1 has a longitudinal central axis A depicted in FIG. 1, which comprises a first shaping part 11 and a second shaping part 12 which are axially spaced from each other, wherein the first shaping part 11 is connected to the second shaping part 12 by a connecting part 13 therebetween to be fixed at a predetermined place. The connecting part 13 may be a hollow structure, which is used to fix the braiding tool 1 properly at the predetermined place. In addition, the space between the first shaping part 11 and the second shaping part 12 can be adjusted by the axial length of the connecting part 13, and thus the axial length of the nasal sinus stent is adjusted. The first shaping part 11 is provided with a plurality of uniformly-distributed first anchor points 111 for hooking the filament in a first plane (also referred to as a first cross section) perpendicular to the longitudinal central axis A. Similarly, the second shaping part 12 is provided with a plurality of uniformly-distributed second anchor points 121 for hooking the filament in a second plane (also referred to as a second cross section) perpendicular to the longitudinal central axis A. In the embodiment shown in FIG. 1, the cross section profiles of the first shaping part 11, connecting part 13 and second shaping part 12 are the same circular, and thus a continuous cylindrical body is formed. In this case, in addition to the first and second shaping parts 11, 12, a third shaping part is formed by the connecting part 13 for determining the final shape of the nasal sinus stent of the present invention. In addition, the cross section of the first anchor point 111 (or the second anchor point 121) can be cylindrical, triangular, square, or semicircle, preferably cylindrical shape. Groove can be formed on the anchor point to receive and facilitate the hook of the filament. Or the anchor points can be upswept, namely the first anchor points 111 (or the second anchor points 121) on the first shaping part 11 (or the second shaping part 12) gradually extend away from the connecting part 13 to facilitate the hook of the filament and avoid the escape of the filament during the braiding and processing procedures, as shown in FIG. 2.

Turning back to FIG. 1, the first anchor points 111 comprise uniformly-spaced anchor points $111_1$, $111_2$, $111_3$, $111_4$, $111_5$ . . . and $111_n$. The second anchor points 121 comprise uniformly-spaced anchor points $121_1$, $121_2$, $121_3$, $121_4$, $121_5$ . . . and $121_n$. An imaginary line connecting the 1st first anchor point $111_1$ to the 1st second anchor point $121_1$ is parallel to the longitudinal central axis A; an imaginary line connecting the 2nd first anchor point $111_2$ to the 2nd second anchor point $121_2$ is parallel to the longitudinal central axis A . . . and an imaginary line connecting the nth first anchor point $111_n$ to the nth second anchor point $121_n$ is parallel to the longitudinal central axis A.

The braiding method provided by the present invention further comprises of braiding a single filament 21 on the braiding tool 1 to form the initial configuration stent 2 by manual or machine. Specifically, around a circumferential direction B (as shown in FIG. 3) of the braiding tool 1, the single filament 21 starts from anyone of the first anchor point 111 (or the second anchor point 121) on the first shaping part 11 (or the shaping part 12). For example, the single filament 21 starts from the 1st first anchor point $111_1$, comes across the connecting part 13 to extend toward the 3rd second anchor point $121_3$, then comes across the connecting part 13 to extend toward the 5th first anchor point $111_5$, so as to complete a first "V" shaped braiding path, and then repeats the "V" shaped braiding path, wherein the anchor points $121_7$, $111_9$ . . . $111_2$, $121_4$ . . . $111_3$, $121_5$ . . . $111_4$, $121_6$ . . . until the single filament returns to the 1st first anchor point $111_1$, to form the initial configuration stent 2.

Figure 4:
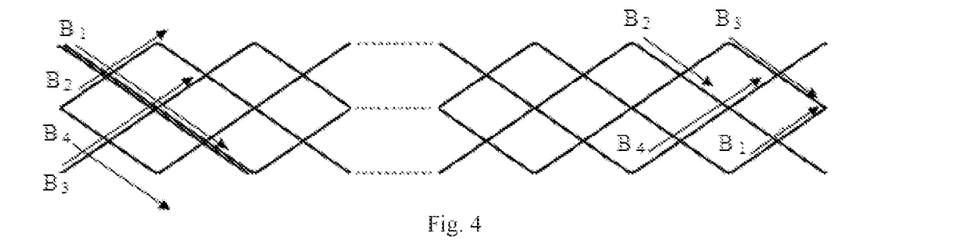
FIG. 4 shows the braiding procedure of the nasal sinus in FIG. 3.
Figure 4A:
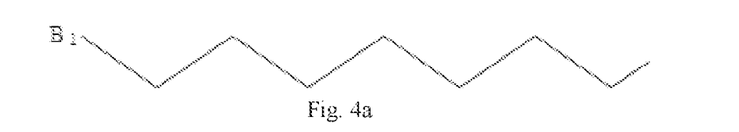
FIG. 4a shows the first circle $B_1$ in FIG. 4.
Figure 4B:
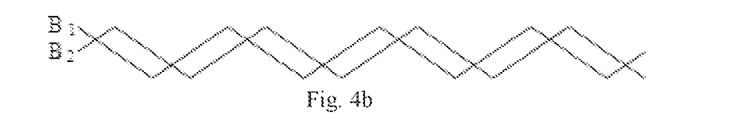
FIG. 4b shows the second circle $B_2$ in FIG. 4.
Figure 4C:
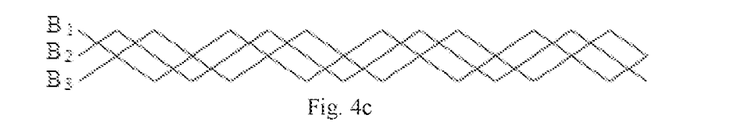
FIG. 4c shows the third circle $B_3$ in FIG. 4.
Figure 4D:
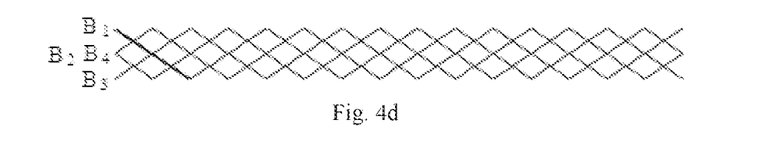
FIG. 4d shows the fourth circle $B_4$ in FIG. 4.
Figure 5:
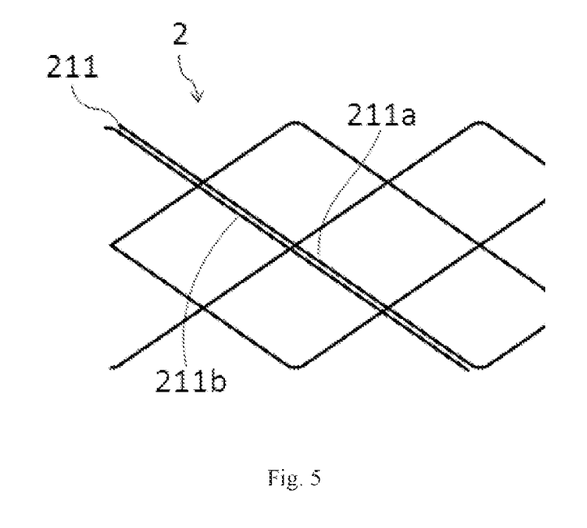
FIG. 5 shows the parallel double lines of the filament ends.

FIG. 4 shows the specific braiding path and indicates that the circumference of the stent is across for four times by one end of the filament 21 to meet the other end as a starting point, so as to complete a whole braiding procedure. A circle means that the circumference is across for one time in the circumferential direction B. In the present embodiment, the first circle $B_1$, the second circle $B_2$, the third circle $B_3$ and the forth circle $B_4$ are provided, wherein the expanded state of the first circle $B_1$ is as shown in FIG. 4a, the expanded state of the second circle $B_2$ is as shown in FIG. 4b, the expanded state of the third circle $B_3$ is as shown in FIG. 4c, and the expanded state of the fourth circle $B_4$ is as shown in FIG. 4d. After all anchor points have been across to finish the braiding procedure, an end-to-end connection is provided by a glue of polymer, a heat weld or the like, as shown in FIG. 5, wherein parallel double lines are formed from ends 211 to strengthen the connection of the starting point 211a and the ending point 211b, and thus to improve the stability of the shape of the stent.

Throughout the braiding procedure, the filament 21 can be interwoven with each other, or can be covering braided. The interweaving means that the filament 21 alternately, above and below, comes across the encountering preceding filament on the braiding path. The covering braiding means that the filament 21 only comes across the encountering preceding filament on the braiding path above. Of course, above two braiding methods can be combined, namely the interweaving and covering braiding can be combined as desired. For example, on the basis of the covering braiding, the last several "V" shaped braiding paths are interwoven. Such interwoven "V" shaped braiding path has a total circumferential distance of at least 50% of the circumference. Sometimes, the distance of the entire circumference is required. The choice of the distance depends on the complexity of the overall pattern of the stent. However, regardless of the pattern of the stent, at least one "V" shaped braiding path is required to be interwoven. Preferably, ends 211 of the filament 21 are interwoven. Although the interweaving is less efficient with respect to the covering braiding, especially by manual, a relatively stable mesh can be formed through the interweaving filament, and the stent is well formed. In addition, an effect of the "pseudo-multilayer" stent can be achieved by the interweaving. In this case, a desired film (e.g., a degradable drug film) can be inserted therebetween, without the need of sewing as a covering stent.

Figure 6:
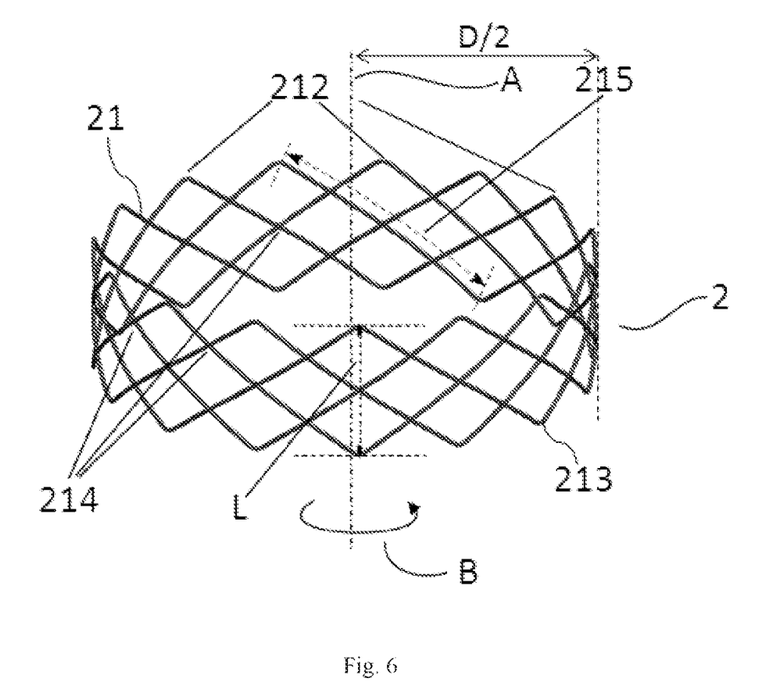
FIG. 6 shows an overall structure diagram of the nasal sinus stent according to embodiment 1.

FIG. 6 is a perspective view of the initial configuration stent 2 formed directly after the completion of the braiding step, wherein the position of the filament 21 corresponding to the first anchor point 111 (or the second anchor point 121) is referred to as the first vertex 212 (or the second vertex 213). The distance between the first vertex 212 and the second vertex 213 is the length L of the initial configuration stent 2. Points of intersection of the filament 21 are referred to as intersections 214. Legs forming the "V" shaped braiding path are referred to as supporting rods 215, wherein the supporting rod 215 extending from the first anchor point 111 to the second anchor point 121 is referred to as a descending supporting rod, and the supporting rod 215 extending from the second anchor point 121 to the first anchor point 111 is referred to as an ascending supporting rod. The initial configuration stent 2 has a diameter D. For a stent with a circular cross-section profile, the diameter D coincides with the diameter of the cross-section circle at that location. For a stent with a non-circular cross-section profile, the diameter D is replaced by a diameter of a circle whose area is equal to the cross-section profile at that location. The length L and diameter D are two of the key factors determining the performance of the stent. The ratio of length L to diameter D is referred to as the aspect ratio L/D. The optional diameter D of the nasal sinus stent according to the present invention ranges from 3 mm to 60 mm, preferably from 15 mm to 60 mm. The optional aspect ratio ranges from 0.1 to 1.9, preferably from 0.1 to 0.5. Since the nasal sinus stent provided by the present invention is based on the adaptation to lesions with irregular shapes, the larger the aspect ratio L/D is, the greater the difference in the performance between the length (axial) direction and the circumferential direction becomes, the greater the anisotropy becomes, and the worse the effect of the adaptation to lesions with irregular shapes becomes. Therefore, the diameter D of the nasal sinus stent of the present invention is relatively close in size to length L. In the prior art, in order to adapt to tubular organ (such as coronary vessel) and to conform to the inner wall of the organ, the stent is usually designed to be elongated and tubular, and the minimum aspect ratio is about 2, usually within 2-30, and commonly within 4-10.

Figure 7:
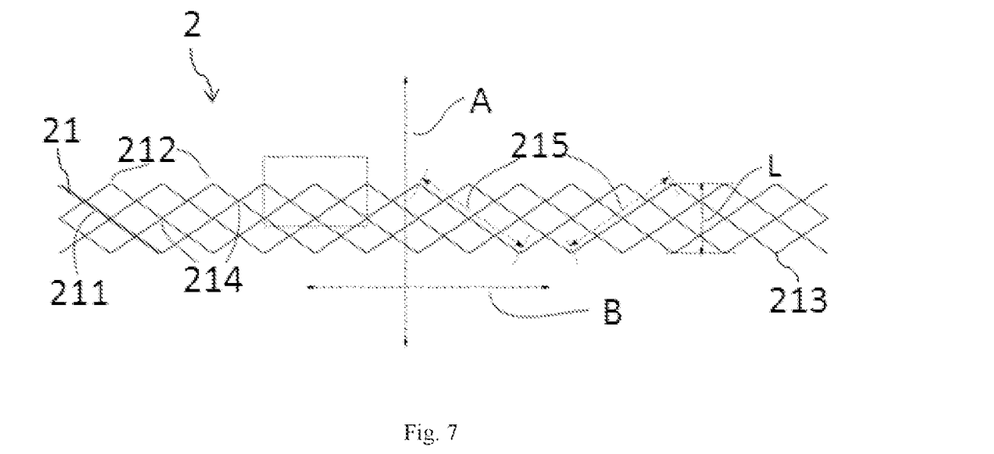
FIG. 7 shows the expanded view of FIG. 6.
Figure 8A:
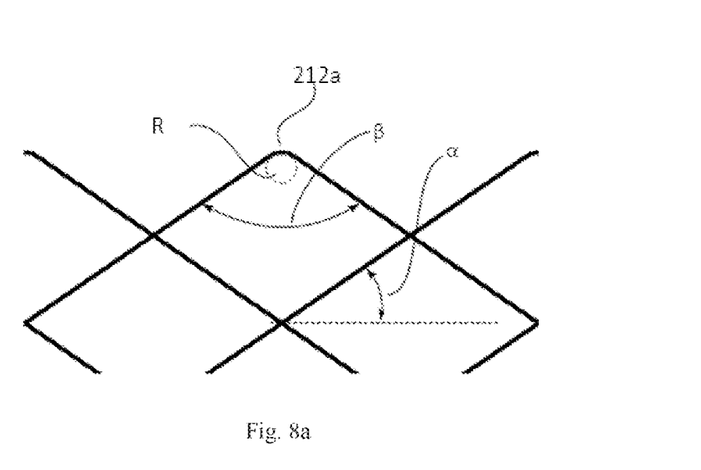
FIG. 8a shows a partial schematic view of the block part in FIG. 7.

FIG. 7 shows an expanded view of the initial configuration stent 2, and FIG. 8a is a partial enlarged view of the block portion in FIG. 7. The angle between the supporting rod 215 and the horizontal direction is referred to as braiding angle α. The angle between the two supporting rods 215 forming the "V" shaped braiding path is referred to vertex angle β. The braiding angle α and vertex angle β play an important role in the performance of the stent. If the vertex angle β is larger and the braiding angle α is smaller, the stent provides higher supporting force, greater rigidity, and more difficult to be compressed. Thus, the stent may be difficult to be compressed to a relative small diameter, and it is difficult to be put into a delivery device. If the vertex angle β is smaller and the braiding angle α is larger, the stent provides greater elasticity, better resilience and smaller support force. Thus, the stent may not play a good supporting role in areas where support is needed. Therefore, proper braiding angle α and vertex angle β are important parameters to ensure the performance of the stent. The braiding angle α of the braiding stent of the present invention ranges from 20° to 70°, and the vertex angle β ranges from 40° to 140°. Preferably, the braiding angle α ranges from 30° to 60°, and the vertex angle β ranges from 60° to 120°.

As shown in FIG. 8a, the first vertex 212 is a curved portion 212a formed by the filament 21 around the first anchor point 111, which provides the stent with compression and self-expansion. Thus, the parameters of the curved portion also affect the performance of the stent. If the radius of the circle R where the curved portion is located (ie, bending radius r of the filament 21 at the anchor point) is too large, the stent will be difficult to be compressed. Namely, the supporting force will be too strong, and the axial ends of the stent are not easily to be compressed. If the radius is too small, the stent can't provide sufficient support. The filament 21 of the present invention has an outer diameter in the range of 0.05 to 3 mm, preferably in the range of 0.1 to 1.5 mm; and the bending radius r of the vertex 212 is 0.5 to 6 times the outer diameter of the filament 21, preferably 1.5 to 4.5 times.

Figure 8B:
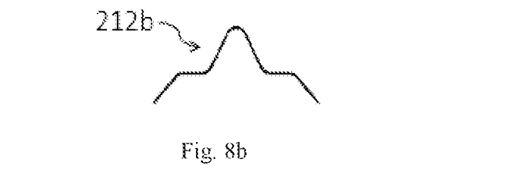
Figure 8C:
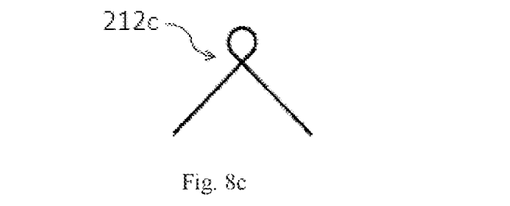
Figure 8D:
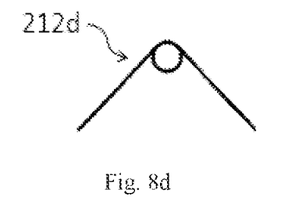
Figure 8E:
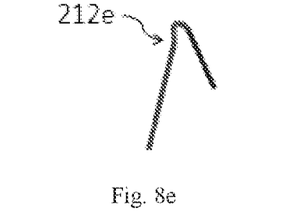

Since the vertices 212, 213 directly affect the elasticity, supporting force and recovery of the stents, the curved portion 212a of the vertices of the stents can be deformed for special effects and purposes. As shown in FIG. 8b, the filament 21 comes across a composite anchor group (shown as five anchor points in the figure) to form a composite vertex 212b with a relatively large circumferential span. Such composite vertex 212b is suitable for a stent with relatively few and sparse vertices, wherein the elasticity and recovery of the vertices are strengthened by the composite vertices 212b. As shown in FIG. 8c, the filament 21 starts below the anchor point and to circle one time around the anchor point forming a negative loop vertex 212c. An intersection of the supporting rods 215 on both sides of the vertex of the stent is formed below the vertex, and next to the negative loop vertex. Since the instability of the stent compression is mainly due to the vertex, the intersection next to the vertex increases the stability of the stent during deformation. Such stent can be easily compressed without the aid of special compression tools. As shown in FIG. 8d, the filament 21 starts above to circle one time around the anchor point to form a positive loop vertex 212d. A spring-like stress can be provided by the positive loop vertex 212d to increase the supporting force and the recovery force after released of the stent. Although the positive loop vertex 212d does not have the intersection below the vertex, the spring formed by the loop binds the supporting rods 215 on both sides of the vertex to twist vertically towards the vertex, which increases the stability of the stent during deformation to some extent. It should be understood that the negative loop vertex 212c (or the positive loop vertex 212d) can also be formed by circling several times around the anchor point. As shown in FIG. 8e, the curved portion formed by the filament 21 around the anchor point can be bent backward or forward to form a tridimensional vertex 212e. An elastic ability is provided in two perpendicular directions respectively by the vertex 212e. Therefore, such stent has better supporting force and recovery than the stent with normal curved portion.

The number of vertices of the initial configuration stent 2 is the same as the number of anchor point. Namely, the initial configuration stent 2 has vertex number n; the initial configuration 2 has circumference C; the vertices 212, 213 divide the circumference C into n equal parts, and the interval between the adjacent first vertices 212 (or the adjacent second vertices 213) is referred to as vertex interval C/n; the circumferential span of the supporting rods 215 is a multiple of the vertex interval C/n, which is referred to as supporting rod spanning vertex interval number m (the descending supporting rod spanning vertex interval number is m1, and the ascending supporting rod spanning vertex interval number is m2), and the circumferential span of each "V" shaped braiding path is denoted in "V" shaped braiding path spanning vertex interval number m1+m2. In the present embodiment, the vertex number n is 15; the supporting rod spanning vertex interval numbers m1, m2 are both equal to 2, and the "V" shaped braiding path spanning vertex interval number m1+m2 is 4; namely, the filament 21 starts from the first anchor point, comes across 2 vertex intervals to extend towards the second anchor point, then comes across 2 vertex intervals to extend towards the first anchor point, so as to complete a "V" shaped braiding path. In fact, the vertex number n according to the nasal sinus stent in the present embodiment can only be an odd number. If the vertex number n is an even number, some of the anchor points will be left and the braiding of the stent can't be completed. Moreover, the vertex number n can't be divisible by the "V" shaped braiding path spanning vertex interval number m1+m2. Otherwise the braiding of the stent can't be completed either. What's more, if the "V" shaped braiding path spanning vertex interval number m1+m2 is a divisor of vertex number n or an integral multiple of the divisor, some of the anchor points will be left and the braiding of the stent can't be completed either.

Figure 9A:
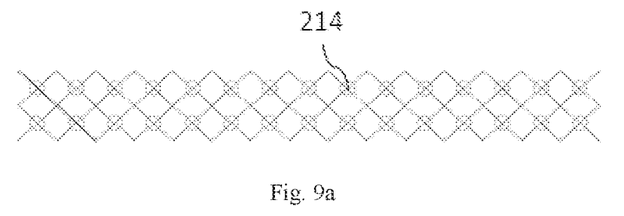
FIG. 9a shows the joint of one embodiment according the present invention.
Figure 9B:
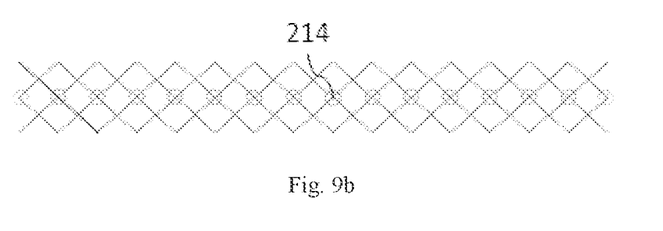
FIG. 9b shows the joint of another embodiment according the present invention.
Figure 9C:
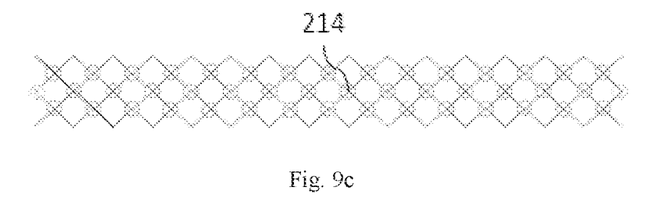
FIG. 9c shows the joint of yet another embodiment according the present invention.
Figure 9D:
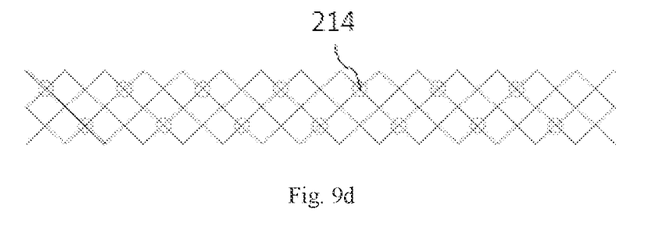
FIG. 9d shows the joint of yet another embodiment according the present invention.
Figure 9E:
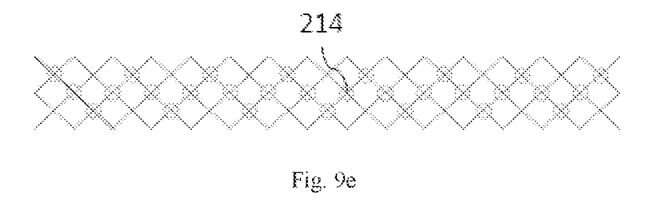
FIG. 9e shows the joint of yet another embodiment according the present invention.

The braiding method provided by the present invention further comprises of connecting the intersections 214 by polymer glue. The polymer glue can be commercially available implantable glue, or can be formulated into a polymer solution by a polymer and a solvent. After the solvent at the intersection is volatilized, the polymer glue is cured. The cured intersections have elasticity, can withstand tensile deformation and are not easily cracked. Thus, the shape of the stent is fixed, and a large deformation capacity at the intersection of the supporting rod is provided. Whether the stent is formed by interweaving or covering braiding, the intersections 214 can be fixed by means of a joint. Specifically, the position of the intersections 214 connected by the joint can be adjusted as desired. FIG. 9a shows the intersections closest to the vertices on both ends of the stent are connected by joints; FIG. 9b shows the intersections at the same cross section in the middle of the stent are connected by joints; FIG. 9c shows all the intersections are connected by joints; FIG. 9d shows the non-adjacent intersections are connected by joints; FIG. 9e shows the intersections along one circumference span of the braiding path are connected by joints.

The braiding method provided by the present invention further comprises of heat-setting the initial configuration stent to form a final configuration stent. Preferably, the initial configuration stent is heat-set under tension, for example, at 120 degrees for 10 minutes. The heating temperature may be the temperature between the glass transition temperature and melting temperature of the filament.

The braiding method provided by the present invention further comprises of forming a drug eluting layer, which may be performed before the braiding step or after the braiding step. For example, a composite filament with sheath-core structure is first formed by coating the filament, and then the composite filament is woven by the braiding tool. For another example, the final configuration stent is first formed by heat-setting, and then the drug eluting layer is loaded on the stent by dipping, spraying, brushing, or the like. The optional drug may be the drug mentioned in CN101945621B, which is incorporated herein by reference in its entirety.

Embodiment 2

The same technical features as those in the embodiment 1 will not be described herein, and only the different steps will be described below.

Figure 10:
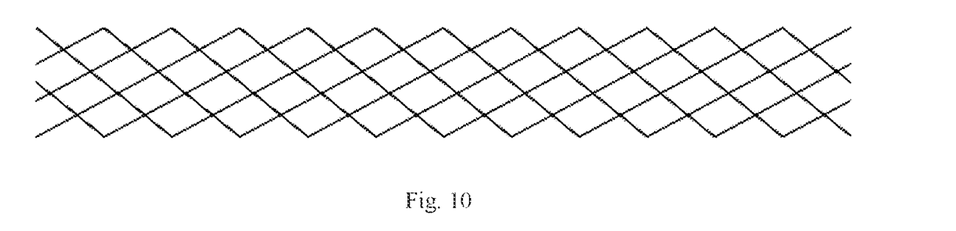
FIG. 10 shows the expanded view of the nasal sinus stent according to embodiment 2 of the present invention.

As shown in FIG. 10, the number of vertices of the initial configuration stent is vertex number 12, and the vertices divide the circumference into 12 equal parts; the circumference of the initial configuration stent is C, and the interval between the adjacent first vertices is vertex interval C/12; wherein the descending supporting rod spanning vertex interval number is 2; the ascending supporting rod spanning vertex interval number is 3, and the circumferential span of each "V" shaped braiding path is denoted in "V" shaped braiding path spanning vertex interval number 5.

Specifically, the filament starts from the 1st first anchor point, comes across 2 vertex intervals to extend towards the second anchor point, then comes across 3 vertex intervals to extend towards the first anchor point, so as to complete a "V" shaped braiding path, and then repeats the "V" shaped braiding path until the filament returns to the 1st first anchor point to form the initial configuration stent.

In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed. For example, when n=10, m1+m2 can't be an integral multiple of the 2 or 5, namely, m1+m2 can't be 2, 4, 5, 6, 8, 10, 12, etc.

Embodiment 3

The same technical features as those in the embodiment 1 will not be described herein, and only the different steps will be described below.

The braiding tool 1' comprises a first shaping part 11' and a second shaping part 12' which are axially spaced from each other. The first shaping part 11' is provided with a plurality of first anchor points 111' for hooking the filament uniformly-distributed in a first cross section. The second shaping part 12' is provided with a plurality of second anchor points 121' for hooking the filament uniformly-distributed in a second cross section. The first anchor points 111' comprises uniformly-spaced anchor point $111_1'$, anchor point $111_2'$, anchor point $111_3'$, anchor point $111_4'$, anchor point $111_5'$ . . . and anchor point $111_n'$. The second anchor points 121' comprises uniformly-spaced anchor point $121_1'$, anchor point $121_2'$, anchor point $121_3'$, anchor point $121_4'$, anchor point $121_5'$ . . . and anchor point $121_n'$. An imaginary line connecting a midpoint of an imaginary line connecting the 1st first anchor point $111_1'$ to the 2nd first anchor point $111_2'$ to the 1st second anchor point $121_1'$ is parallel to the longitudinal central axis A . . . an imaginary line connecting a midpoint of an imaginary line connecting the (n-1)th first anchor point $111_{n-1}'$ to the nth first anchor point $111_n'$ to the (n-1)th second anchor point $121_n-1'$ is parallel to the longitudinal central axis A; an imaginary line connecting a midpoint of an imaginary line connecting the nth first anchor point $111_n'$ to the 1st first anchor point $111_1'$ to the nth second anchor point $121_n'$ is parallel to the longitudinal central axis A.

Figure 11:
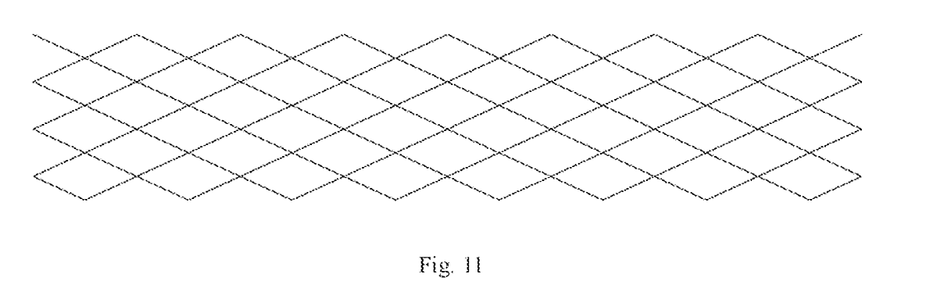
FIG. 11 shows the expanded view of the nasal sinus stent according to embodiment 3 of the present invention.

As shown in FIG. 11, the number of vertices of the initial configuration stent is vertex number 8, and the vertices divide the circumference into 8 equal parts; the circumference of the initial configuration stent is C, and the interval between the adjacent first vertices is vertex interval C/8 (is referred to as); wherein the descending supporting rod spanning vertex interval number is 3.5; the ascending supporting rod spanning vertex interval number is 3.5, and the circumferential span of each "V" shaped braiding path is denoted in "V" shaped braiding path spanning vertex interval number 7.

Specifically, the filament starts from the 1st first anchor point, comes across 3.5 vertex intervals to extend towards the second anchor point, then comes across 3.5 vertex intervals to extend towards the first anchor point, so as to complete a "V" shaped braiding path, and then repeats the "V" shaped braiding path until the filament returns to the 1st first anchor point to form the initial configuration stent.

In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 4

The same technical features as those in the embodiment 3 will not be described herein, and only the different steps will be described below.

Figure 12:
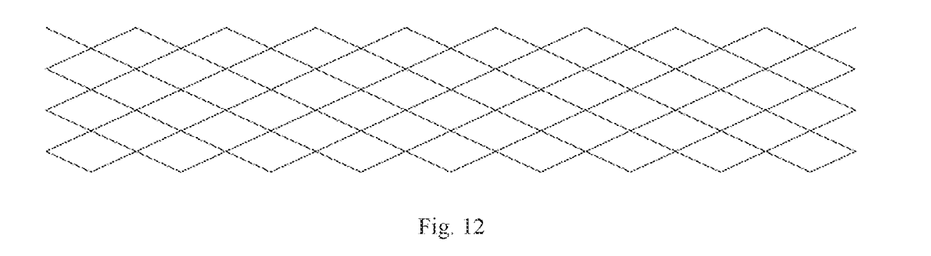
FIG. 12 shows the expanded view of the nasal sinus stent according to embodiment 4 of the present invention.

As shown in FIG. 12, the number of vertices of the initial configuration stent is vertex number 9, and the vertices divide the circumference into 9 equal parts; the circumference of the initial configuration stent is C, and the interval between the adjacent first vertices is vertex interval C/9; wherein the ascending supporting rod spanning vertex interval number is 3.5; the descending supporting rod spanning vertex interval number is 3.5, and the circumferential span of each "V" shaped braiding path is denoted in "V" shaped braiding path spanning vertex interval number 7.

Specifically, the filament starts from the 1st first anchor point, comes across 3.5 vertex intervals to extend towards the second anchor point, then comes across 3.5 vertex intervals to extend towards the first anchor point, so as to complete a "V" shaped braiding path, and then repeats the "V" shaped braiding path until the filament returns to the 1st first anchor point to form the initial configuration stent.

In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 5

The same technical features as those in the embodiment 3 will not be described herein, and only the different steps will be described below.

Figure 13:
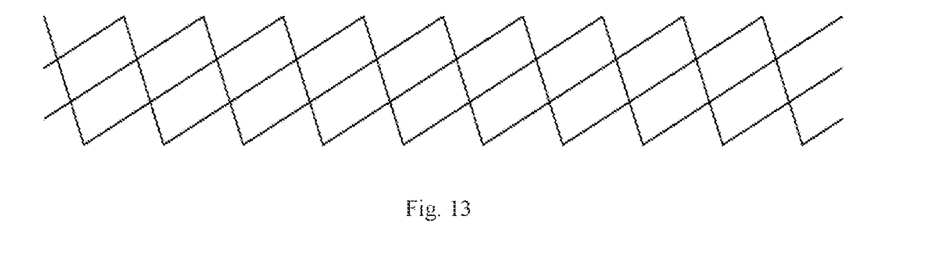
FIG. 13 shows the expanded view of the nasal sinus stent according to embodiment 5 of the present invention.

As shown in FIG. 13, the number of vertices of the initial configuration stent is vertex number 10, and the vertices divide the circumference into 10 equal parts; the circumference of the initial configuration stent is C, and the interval between the adjacent first vertices is vertex interval C/10; wherein the descending supporting rod spanning vertex interval number is 0.5; the ascending supporting rod spanning vertex interval number is 2.5, and the circumferential span of each "V" shaped braiding path is denoted in "V" shaped braiding path spanning vertex interval number 3.

Specifically, the filament starts from the 1st first anchor point, comes across 0.5 vertex intervals to extend towards the second anchor point, then comes across 2.5 vertex intervals to extend towards the first anchor point, so as to complete a "V" shaped braiding path, and then repeats the "V" shaped braiding path until the filament returns to the 1st first anchor point to form the initial configuration stent.

In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 6

The same technical features as those in the embodiment 3 will not be described herein, and only the different steps will be described below.

Figure 14:
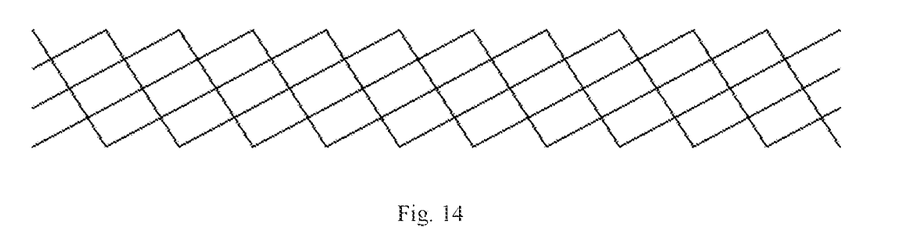
FIG. 14 shows the expanded view of the nasal sinus stent according to embodiment 6 of the present invention.

As shown in FIG. 14, the number of vertices of the initial configuration stent is vertex number 11, and the vertices divide the circumference into 11 equal parts; the circumference of the initial configuration stent is C, and the interval between the adjacent first vertices is vertex interval C/11; wherein the descending supporting rod spanning vertex interval number is 1; the ascending supporting rod spanning vertex interval number is 3, and the circumferential span of each "V" shaped braiding path is denoted in "V" shaped braiding path spanning vertex interval number 4.

Specifically, the filament starts from the 1st first anchor point, comes across 1 vertex interval to extend towards the second anchor point, then comes across 3 vertex intervals to extend towards the first anchor point, so as to complete a "V" shaped braiding path, and then repeats the "V" shaped braiding path until the filament returns to the 1st first anchor point to form the initial configuration stent. In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 7

The same technical features as those in the embodiment 1 will not be described herein, and only the different steps will be described below.

Figure 15:
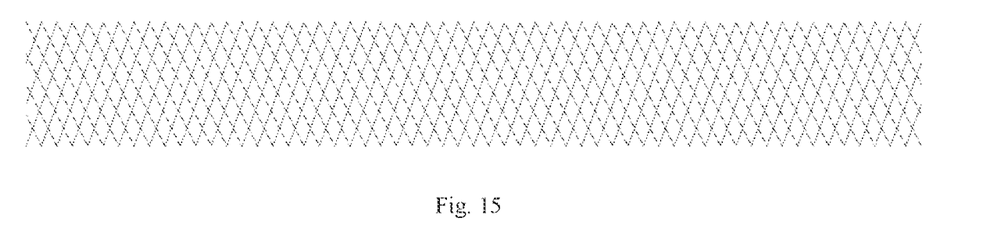
FIG. 15 shows the expanded view of the nasal sinus stent according to embodiment 7 of the present invention.

As shown in FIG. 15, the number of vertices of the initial configuration stent is vertex number 58, and the vertices divide the circumference into 58 equal parts; the circumference of the initial configuration stent is C, and the interval between the adjacent first vertices is vertex interval C/58; wherein the descending supporting rod spanning vertex interval number is 4; the ascending supporting rod spanning vertex interval number is 3, and the circumferential span of each "V" shaped braiding path is denoted in "V" shaped braiding path spanning vertex interval number 7.

Specifically, the filament starts from the 1st first anchor point, comes across 4 vertex intervals to extend towards the second anchor point, then comes across 3 vertex intervals to extend towards the first anchor point, so as to complete a "V" shaped braiding path, and then repeats the "V" shaped braiding path until the filament returns to the 1st first anchor point to form the initial configuration stent In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 8

The same technical features as those in the embodiment 3 will not be described herein, and only the different steps will be described below.

Figure 16:
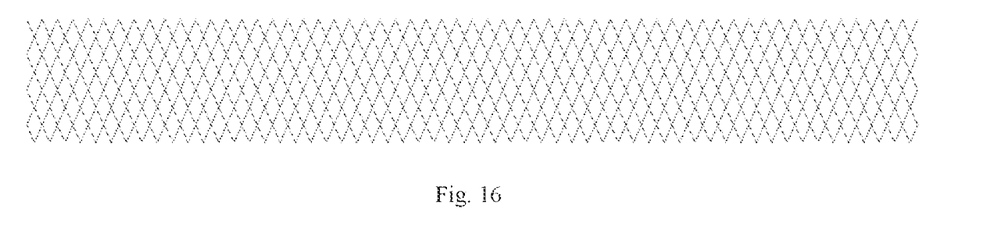
FIG. 16 shows the expanded view of the nasal sinus stent according to embodiment 8 of the present invention.

As shown in FIG. 16, the number of vertices of the initial configuration stent is vertex number 58, and the vertices divide the circumference into 58 equal parts; the circumference of the initial configuration stent is C, and the interval between the adjacent first vertices is vertex interval C/58; wherein the descending supporting rod spanning vertex interval number is 4.5; the ascending supporting rod spanning vertex interval number is 3.5, and the circumferential span of each "V" shaped braiding path is denoted in "V" shaped braiding path spanning vertex interval number 8.

Specifically, the filament starts from the 1st first anchor point, comes across 4.5 vertex intervals to extend towards the second anchor point, then comes across 3.5 vertex intervals to extend towards the first anchor point, so as to complete a "V" shaped braiding path, and then repeats the "V" shaped braiding path until the filament returns to the 1st first anchor point to form the initial configuration stent.

In fact, the vertex number n according to the nasal sinus stent in the present embodiment may be an odd number or an even number. However, the vertex number n according to the nasal sinus stent in the present embodiment can't be divisible by the "V" shaped braiding path spanning vertex interval number m1+m2. Otherwise the braiding of the stent can't be completed. What's more, if the "V" shaped braiding path spanning vertex interval number m1+m2 is a divisor of vertex number n or an integral multiple of the divisor, some of the anchor points will be left and the braiding of the stent can't be completed.

Embodiment 9

The profile of the braiding tool coincides with that of the initial configuration stent as those in the embodiment 1. However, the profile of the braiding tool is not a cylindrical body, and the profile of the corresponding initial configuration stent is not a cylindrical body as shown in FIG. 6. The profile of the initial configuration stent will be described below, and the description of the corresponding braiding tool is omitted here.

Figure 17:
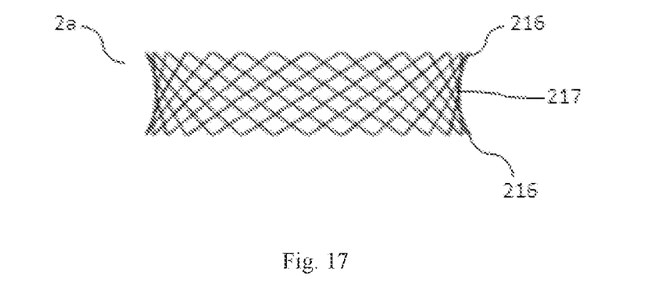
FIG. 17 shows the overall structure diagram of the nasal sinus stent according to embodiment 9 of the present invention.

As shown in FIG. 17, the initial configuration stent $2a$ is big at both ends but small in the middle. Namely, the diameters of the ends 216 of the initial configuration stent $2a$ are larger than the diameter of the middle 217. In the present embodiment, the diameter of the initial configuration stent $2a$ increases gradually from the middle 217 towards the ends 216. The formed stent is also referred to as a flared stent, wherein the two ends can be formed as positioning portion to relatively fix the stent to the lesion.

Embodiment 10

The first shaping part and the second shaping part of the braiding tool have the same cross sectional profile and are circular as those in the embodiment 1. However, the cross sectional profile of the connecting part is smaller than that of the first shaping part (or the second shaping part). In addition, the braiding tool of the present embodiment further comprises a hoop around and spaced from the connecting part. Specifically, the filament starts from the 1st first anchor point, comes across m1 vertex intervals to extend towards the second anchor point between the hoop and the connecting part, then comes across m2 vertex intervals to extend towards the first anchor point between the hoop and the connecting part, so as to complete a first "V" shaped braiding path, and then repeats the "V" shaped braiding path until the filament returns to the 1st first anchor point to form the initial configuration stent $2b$.

Figure 18:
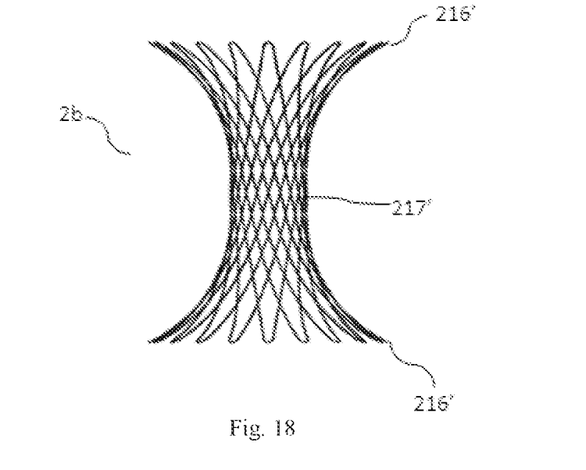
FIG. 18 shows the overall structure diagram of the nasal sinus stent according to embodiment 10 of the present invention.

As shown in FIG. 18, the initial configuration stent $2b$ is big at both ends but small in the middle. Namely, the diameters of the ends 216' of the initial configuration stent $2b$ are larger than the diameter of the middle 217'. In the present embodiment, the diameter of the initial configuration stent $2b$ increases gradually from the middle 217' towards the ends 216'. The formed stent is also referred to as a flared stent, wherein the two ends can be formed as positioning portion to relatively fix the stent to the lesion.

Embodiment 11

The profile of the braiding tool coincides with that of the initial configuration stent as those in the embodiment 1. However, the profile of the braiding tool is not a cylindrical body, and the profile of the corresponding initial configuration stent is not a cylindrical body as shown in FIG. 6. The profile of the initial configuration stent will be described below, and the description of the corresponding braiding tool is omitted here.

Figure 19:
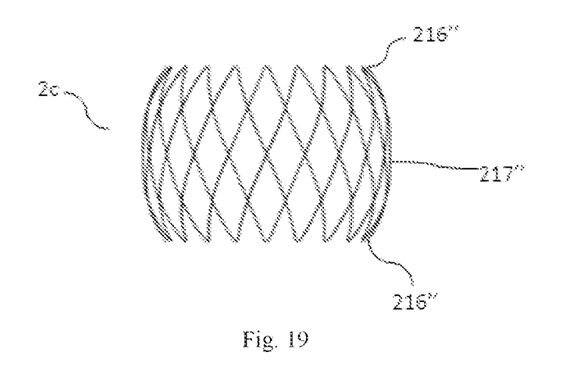
FIG. 19 shows the overall structure diagram of the nasal sinus stent according to embodiment 11 of the present invention.

As shown in FIG. 19, the initial configuration stent $2c$ is small at both ends but big in the middle. Namely, the diameters of the ends 216" of the initial configuration stent $2c$ are smaller than the diameter of the middle 217". In the present embodiment, the diameter of the initial configuration stent $2c$ decreases gradually from the middle 217" towards the ends 216". The formed stent is also referred to as convergent stent, tending to be an elliptical-shaped, egg-shaped, or even spherical-shaped stent, which can be placed in a cavity closing to a circular space.

Embodiment 12

The profile of the braiding tool coincides with that of the initial configuration stent as those in the embodiment 1. However, the profile of the braiding tool is not a cylindrical body, and the profile of the corresponding initial configuration stent is not a cylindrical body as shown in FIG. 6. The profile of the initial configuration stent will be described below, and the description of the corresponding braiding tool is omitted here.

Figure 20:
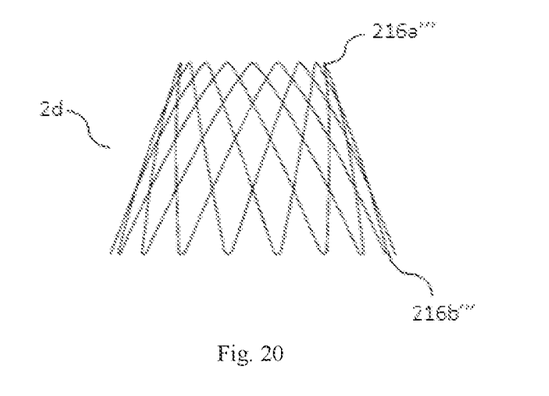
FIG. 20 shows the overall structure diagram of the nasal sinus stent according to embodiment 12 of the present invention.

As shown in FIG. 20, the initial configuration stent $2d$ is conical frustum shaped. Namely, the diameter of the first end 216a''' of the initial configuration stent $2d$ is smaller than the diameter of the second end 216b'''. In the present embodiment, the diameter of the initial configuration stent $2d$ increases gradually from the first end 216a''' towards the second end 216b'''. The formed stent has a slow transition of the supporting force along the axial direction, which does not have a poor radical force at ends of the convergent stent.

The braiding tool in the present embodiment is conical frustum shaped. It is known that the conical frustum is a geometry formed by the rotation of a right trapezoid, wherein the leg perpendicular to the base defines the rotation axis, and the geometry is enclosed by the surfaces formed by the other leg and bases. The rotation axis is referred to as the axis of the conical frustum. The round surfaces formed by the rotation of the top and bottom bases are referred to as the top and bottom faces of the conical frustum. The curved surface formed by the rotation of the other leg is referred to as lateral face the conical frustum. The leg of the right trapezoid on the lateral face is referred to as the generatrix of the conical frustum. In the present embodiment, the axis of the conical frustum is the longitudinal central axis A of the braiding tool; the imaginary line connecting the nth first anchor point ($111_n$) in the first anchor points ($111_1$, $111_2$ . . . $111_n$) to the nth second anchor point ($121_n$) in the second anchor points ($121_1$, $121_2$ . . . $121_n$) is the generatrix of the conical frustum, thus the first vertices and the second vertices are aligned on the lateral face of the conical frustum.

In another embodiment, the imaginary line connecting the midpoint of the imaginary line connecting the (n−1)th first anchor point ($111_{n-1}$) to the nth first anchor point ($111_n$) in the first anchor points ($111_1$, $111_2$ . . . $111_n$) to and the (n−1)th second anchor point ($121_{n-1}$) in the second anchor points ($121_1$, $121_2$ . . . $121_n$) is the generatrix of the conical frustum, thus the first vertices and the second vertices alternate on the lateral face of the conical frustum.

When stents as shown in FIGS. 17-19 are in complete longitudinal symmetry, the first anchor points and the second anchor points are distributed on the same cylindrical surface.

The first vertices and the second vertices can be aligned as embodiment 1, namely the imaginary line connecting the nth first anchor point ($111_n$) in the first anchor points ($111_1$, $111_2 \ldots 111_n$) to the nth second anchor point ($121_n$) in the second anchor points ($121_1$, $121_2 \ldots 121_n$) is parallel to the longitudinal central axis A. Also, the first vertices and the second vertices can alternate as embodiment 3, namely the imaginary line connecting the midpoint of the imaginary line connecting the (n-1)th first anchor point ($111_{n-1}$) to the nth first anchor point ($111_n$) in the first anchor points ($111_1$, $111_2 \ldots 111_n$) to and the (n-1)th second anchor point ($121_{n-1}$) in the second anchor points ($121_1$, $121_2 \ldots 121_n$) is parallel to the longitudinal central axis A.

When stents as shown in FIGS. 17-19 are not in complete longitudinal symmetry, the first anchor points and the second anchor points are not distributed on the same cylindrical surface, and the first anchor points and the second anchor points will be distributed on the lateral face of the conical frustum. Referring to embodiment 12, the first vertices and the second vertices align on the lateral face of the conical frustum, namely the imaginary line connecting the nth first anchor point ($111_n$) in the first anchor points ($111_1$, $111_2 \ldots 111_n$) to the nth second anchor point ($121_n$) in the second anchor points ($121_1$, $121_2 \ldots 121_n$) is the generatrix of the conical frustum. The first vertices and the second vertices can alternate, namely the imaginary line connecting the midpoint of the imaginary line connecting the (n-1)th first anchor point ($111_{n-1}$) to the nth first anchor point ($111_n$) in the first anchor points ($111_1$, $111_2 \ldots 111_n$) to and the (n-1)th second anchor point ($121_{n-1}$) in the second anchor points ($121_1$, $121_2 \ldots 121_n$) is the generatrix of the conical frustum.

In addition to the specific shapes recited in the above embodiments, the profile of the braiding tool can be a cylinder, a truncated cone, a sphere, an ellipsoid, a square, or a capsule. It should be understood that when the cross sectional profiles of the first shaping part, the connecting part and the second shaping part are not uniform, generally, the cross sectional profile of the connecting part is smaller than that of the first (or second) shaping part. However, the cross sectional profile of the connecting part can also be larger than that of the first shaping part (or the second shaping part), and the anchor points are correspondingly set to be upswept (as shown in FIG. 2) to hook up the filament and avoid the escape of the filament.

The above preferred embodiments of the present invention are not intended to limit the scope of the present invention. Obviously, many variations of the present invention are possible. The simple and equivalent changers and modifications in light of the above teachings fall within the scope of the appended claims. What has not been described in detail in the present invention are all routine technical means.

What is claimed is:

1. A braiding method for a nasal sinus stent, the braiding method comprising:
   providing a filament;
   providing a braiding tool having a longitudinal central axis, wherein the weaving tool comprises a first shaping part and a second shaping part which are axially spaced from each other; wherein the first shaping part is provided with n uniformly-spaced first anchor points (1111, 1112 . . . 111n) for hooking the filament in a first cross section perpendicular to the longitudinal central axis; the second shaping part is provided with n uniformly-spaced second anchor points (1211, 1212 . . . 121n) for hooking the filament in a second cross section perpendicular to the longitudinal central axis; wherein n is an integer in 3-59;
   forming an initial configuration stent around a circumferential direction of the weaving tool, by allowing a single filament starting from a 1st first anchor point (1111) on the first shaping part, coming across m1 vertex intervals to extend towards the second anchor point, and then coming across m2 vertex intervals to extend towards the first anchor point, so as to complete a first "V" shaped braiding path, and then repeating the "V" shaped braiding path until the single filament returns to the 1st first anchor point (1111), wherein the initial configuration stent has a circumference and n vertices; m1 and m2 are integral multiples of 0.5, the sum of m1+m2 is an integer, and the sum of m1+m2 is not an integral multiple of a divisor of n, and wherein the divisor of n is not equal to 1.

2. The braiding method according to claim 1, wherein the nth first anchor point (111n) of the first anchor points (1111, 1112 . . . 111n) is staggered or aligned with the nth second anchor point (121n) of the second anchor points (1211, 1212 . . . 121n) on a cylindrical surface.

3. The braiding method according to claim 1, wherein the nth first anchor point (111n) of the first anchor points (1111, 1112 . . . 111n) is staggered or aligned with the nth second anchor point (121n) of the second anchor points (1211, 1212 . . . 121n) on a lateral face of a conical frustum.

4. The braiding method according to claim 1, wherein an imaginary line connecting the nth first anchor point (111n) of the first anchor points (1111, 1112 . . . 111n) to the nth second anchor point (121n) of the second anchor points (1211, 1212 . . . 121n) is parallel to the longitudinal central axis.

5. The braiding method according to claim 4, wherein when m1=m2, n is an odd number in 3-59.

6. The braiding method according to claim 1, wherein an imaginary line connecting a midpoint of an imaginary line connecting the (n-1)th first anchor point (111n-1) of the first anchor points (1111, 1112 . . . 111n) to the nth first anchor point (111n) to the (n-1)th second anchor point (121n-1) of the second anchor points (1211, 1212 . . . 121n) is parallel to the longitudinal central axis.

7. The braiding method according to claim 1, wherein the filament is a monofilament or a strand forming by twisting at least two monofilaments with each other.

8. The braiding method according to claim 1, wherein the braiding tool further comprises a connecting part, wherein the first shaping part is connected to the second shaping part by the connecting part to be fixed at a predetermined place.

9. The braiding method according to claim 8, wherein the weaving tool further comprises a hoop around and spaced from the connecting part.

10. The braiding method according to claim 9, wherein the single filament starts from the 1st first anchor point (1111) on the first shaping part, comes across m1 vertex intervals to extend towards the 1st second anchor point between the connecting part and the hoop, comes across m2 vertex intervals to extend towards the first anchor point between the connecting part and the hoop, so as to complete a first "V" shaped braiding path, and then repeats the "V" shaped braiding path until the single filament returns to the 1st first anchor point (1111) to form the initial configuration stent.

11. The braiding method according to claim 1, wherein an end-to-end connection is provided by parallel double lines formed from ends of the single filament.

12. The braiding method according to claim 1, wherein the filament has intersections connected by polymer glue.

* * * * *